United States Patent [19]

Goettsche et al.

[11] Patent Number: 5,078,912

[45] Date of Patent: Jan. 7, 1992

[54] WOOD PRESERVATIVE

[75] Inventors: Reimer Goettsche, Baden-Baden; Hans-Norbert Marx, Buehl-Weitenung; Wendelin Hettler, Sinzheim-Muellhofen; Richard Stanek, Mainz-Finthen; Hans-Peter Heidenreich, Baden-Baden, all of Fed. Rep. of Germany

[73] Assignee: Dr. Wolman GmbH, Sinzheim, Fed. Rep. of Germany

[21] Appl. No.: 523,282

[22] Filed: May 1, 1991

Related U.S. Application Data

[63] Continuation of Ser. No. 334,791, Apr. 6, 1989, abandoned, which is a continuation of Ser. No. 172,981, Mar. 23, 1988, abandoned, which is a continuation of Ser. No. 870,905, Jun. 5, 1986, abandoned.

[51] Int. Cl.⁵ .................... C09K 15/18; C09K 15/32
[52] U.S. Cl. ............... 252/400.53; 252/400.1; 252/400.4; 252/602; 252/607; 427/439; 427/440; 427/351; 427/370; 427/305; 427/317; 106/15.05
[58] Field of Search ............ 252/607, 602, 400.1, 252/400.53, 400.4; 427/439, 440, 351, 370, 305, 317; 106/15.05

[56] References Cited

U.S. PATENT DOCUMENTS

| | | | |
|---|---|---|---|
| 2,041,655 | 5/1936 | Gunn | 134/78.6 |
| 3,976,594 | 8/1976 | Dahlgren | 252/400.52 |
| 4,143,153 | 3/1979 | Pommer et al. | 424/289 |
| 4,288,249 | 9/1981 | Amundsen et al. | 106/18.35 |
| 4,382,884 | 5/1983 | Rohringer et al. | 252/606 |
| 4,420,542 | 12/1983 | Sowers | 428/541 |
| 4,461,721 | 7/1984 | Goettsche et al. | 252/607 |

*Primary Examiner*—Deborah L. Kyle
*Assistant Examiner*—Valarie Fee
*Attorney, Agent, or Firm*—Keil & Weinkauf

[57] ABSTRACT

An agent for impregnating solid wood by the pressure process, based on a water-dilutable formulation of a copper salt, excess alkanolamine and, if required, a salt with a fungicidal anion, has a pH of not less than 8 in the concentration usually employed and corresponding to about 1–5% by weight of non-aqueous components in the aqueous solution.

4 Claims, No Drawings

WOOD PRESERVATIVE

This application is a continuation of Ser. No. 07/334,791, filed Apr. 6, 1989, now abandoned, which is a continuation of Ser. No. 07/172,981, filed Mar. 23, 1988, now abandoned, which is a continuation of Ser. No. 06/870,905, filed June 5, 1986, now abandoned.

The present invention relates to the provision of agents for the pressure impregnation of (solid) wood, which are based on aqueous formulations of a copper salt, an alkanolamine and, if required, further components, in particular fungicidal salts whose action is attributable to the anion, for example salts of boric acid.

To date, chromate-containing, fixing wood preservatives have been employed for protecting wood which is exposed to weathering or humidity or, as part of a structure, is in contact with earth. These wood preservatives are used in the form of aqueous solutions, e.g. from 2 to 6% solutions, depending on the level of risk to which the impregnated wood is subsequently exposed, the treatment being carried out with the aid of large industrial impregnation plants (pressure impregnating process).

For use in contact with earth, the agents used are exclusively those which contain not only chromate but also copper, owing to the fact that they have to be effective against wood rot caused by fungi. A distinction is made between the CC type (based on copper and chromium), the CCB type (based on copper, chromium and boron), the CCF type (based on copper, chromium and fluorine) and the CCA type (based on copper, chromium and arsenic).

Fixing in these wood preservatives is via the chromate part. After impregnation, the chromates react with the constituents of the wood and are reduced to trivalent chromium compounds; as a result, the pH in the wood increases so that copper compounds and chromium compounds are precipitated in the wood as water-insoluble compounds and are fixed.

However, chromates, i.e. hexavalent chromium compounds, constitute a considerable risk for the environment when leakage or weather effects during the fixing process result in these compounds being washed out, so that surface water, ground water and tap water are contaminated. The maximum concentration currently tolerated is, for example, 0.05 ppm. Even if the chromium in the wood is present in trivalent form, it can, by oxidation, be converted to hexavalent chromium compounds, which may then be washed out of the ash; this gives rise to problems with regard to disposal.

To date, chromium-free, copper-containing, water-soluble wood preservatives for large-scale industrial impregnation have been proposed, in which, for example, copper arsenate and borate are converted to a water-soluble alkaline form by complex formation with ammonia. These agents are fixed in the wood by evaporating the ammonia and as a result of buffering with wood constituents (the pH of the wood itself is about 5). Apart from the odor nuisance, these impregnating solutions, or the concentrates, may lose their stability through the evaporation of the ammonia, so that the solutions are no longer suitable for further impregnation. Furthermore, when the ammonia content is insufficient, penetration of the preservative into the wood is hindered.

Amines having good complexing properties, e.g. ethylenediamine, have also been recommended for wood preservatives containing copper and fluorine, for the protection of wood-based materials, e.g. particle boards. These agents are mixed into the resin in highly concentrated form and, together with the resin, are sprayed onto the chips. They are unsuitable for preserving solid wood since the ethylenediamine complexes are stable, even at the pH of the wood itself (5-6) and do not fix; they are washed out of the wood by water.

Copper is fixed only when water-insoluble organic copper salts can form. For example, wood preservatives which contain copper salts of N-nitrosocyclohexylhydroxylamine (new name: copper salt of N-cyclohexyldioxydiazenium oxide, Cu-HDO) have been described. The Cu-HDO is converted, via polyamines, e.g. ethylenediamine or diethylenetriamine, into wood preservative concentrates, which are dissolved in water in order to carry out impregnation. They become fixed in the wood as a result of buffering with the aid of wood constituents from about pH 7.5. However, this fixing takes place so rapidly that penetration of the Cu-HDO is prevented during pressure impregnation. For example, even in the case of pine, which can be easily impregnated, the Cu-HDO only penetrates an outer layer of about 10-15 mm. Dispersing of the preservative toward the inside falls off rapidly.

If other amines, e.g. alkanolamines, in particular monoethanolamine, are used for complexing, the Cu-HDO is completely dissolved only in highly concentrated solutions; dilution with water to the concentration for use precipitates it once again.

We have found that the disadvantages described above can be overcome if water-dilutable agents obtained from (water-soluble or insoluble), (inorganic) copper compounds, e.g. copper sulfate, copper fluoroborate, copper hydroxide, copper borate, copper fluoride, copper carbonate or copper oxychloride, with complex formation with alkanolamines in aqueous solution are used; when the agent is diluted to produce the ready-to-use form, the pH must be brought to 8 or higher.

The water-dilutable agents contain the copper in concentrated form, in general in an amount of from 1 to 15% by weight, calculated as the element.

Suitable concentrates contain, for example, from 5 to 50% by weight of a copper salt, from 5 to 50% by weight of an alkanolamine, up to 50% by weight of a salt of a fungicidal anion and up to 5% by weight of free alkali, the percentages summing to 100, and, if desired, minor amounts of other components, such as amines, ammonia, corrosion inhibitors and, if required, water, the amount of which can, however, generally be kept small and essentially facilitates handling. However, the present invention also relates to the impregnating solutions of appropriately lower specific concentrations, these solutions being prepared by dilution with water.

Complexing can be carried out in the presence of fungicidal anions, e.g. borates or fluorides. Dissolving the copper compounds in the alkanolamine, in particular monoethanolamine, if necessary with the addition of water, gives highly concentrated water-soluble pastes or liquid concentrates which, when dissolved in water, can be used for impregnating wood. The pH of the aqueous impregnating solutions is 8 or higher, in particular from 9 to 10 (concentration-dependent). When impregnation is carried out by the pressure process, the copper component penetrates thoroughly into the wood. During the impregnation process, the novel preservatives are buffered by the wood acids present in the wood, the copper being precipitated in the wood from about pH 7. From pH 7-7.5, the complex-forming power of the alkanolamines is in fact no longer sufficient to keep the copper in solution, so that the copper is fixed. The extent to which the copper is fixed is of the same order of magnitude as for the previous chromate-containing and copper-containing wood preservatives, i.e. not less than 85%, and on average from 90 to 95%, of the copper component is fixed in the wood. Fixing is partly dependent on the additional alkanolamine content which is required for adjusting the pH in the case of strong acids or fungicidal anions; a certain effect in respect of pH shift can, however, also be achieved by adding, for example, an alkali metal hydroxide solution, for example sufficient to produce a pH shift of up to about 1. In general, this measure applies to the amount of fungicidal anions or acid radicals; it can also be brought to the required pH, independently of complex formation, by an alkali, ammonia or another water-soluble amine.

For economic reasons, a particularly suitable complexing agent is monoethanolamine. The novel wood preservatives may also be prepared using other alkanolamines, e.g. isopropanolamine, 1,1- or 1,2-diaminoethanol, aminoethylethanolamine, diethanolamine, dimethylethanolamine, etc. The amount of alkanolamines added is such that it is sufficient for complex formation with copper (1 g atom of copper generally requires 4 mol equivalents of amine) and, if necessary, for forming alkanolamine salts of the fungicidal anions additionally used (fluoride, borate or fluoroborate) or esters, so that the aqueous impregnating solution is brought to a pH of 8 or higher, preferably from 9 to 10.

To test the invention in practice, the following procedure was adopted: the concentrates, in the amount stated in each case (4 or 3%) were diluted with water, and the product was used to impregnate small pine blocks.

After drying, the stated blocks were washed for 4 weeks with distilled water, the water being changed daily. The amount of copper washed out was then determined.

EXAMPLE 1

A mixture of
33.3% by weight of $CuSO_4.5H_2O$,
33.3% by weight of monoethanolamine and
33.4% by weight of water
is dissolved in water in a concentration of 40 g per liter of water (referred to below as 4% strength solution).
Amount of copper washed out 7.5%.

EXAMPLE 2

20.0% by weight of $3Cu(OH)_2.CuCl_2$,
40.5% by weight of monoethanolamine and
40.0% by weight of water
(4% strength aqueous solution).
Amount of copper washed out 10.5%.

EXAMPLE 3

15.0% by weight of $Cu(OH)_2.CuCO_3$,
16.0% by weight of monoethanolamine,
16.0% by weight of aminoethylethanolamine,
25.0% of $H_3BO_3$ and
38.0% of $H_2O$
(4% strength aqueous solution).
Amount washed out:
Cu 10.5%
B 85.5%.

EXAMPLE 4

13.5% of $Cu(OH)_2$,
25.0% of boric acid,
17.5% of monoethanolamine,
17.5% of aminopropanol and
26.5% of water
(4% strength aqueous solution).
Amount washed out:
Cu 7.7%
B 86.5%.

EXAMPLE 5

50% of $CU(BF_4)_2$ solution (dissolved in water to give a 50% strength solution),
30% of monoethanolamine and
20% of $H_2O$
(3% strength aqueous solution, defined as above).
Amount washed out:
Cu 10.5%
F 70.0%
B 75.0%.

EXAMPLE 6

16.5% of $Cu(OH)_2.CuCO_3$,
10% of $NH_4HF_2$,
36.0% of monoethanolamine and
3.5% of $H_2O$
(3% strength aqueous solution).
Amount washed out:
Cu 0.5%
F 78.5%.

EXAMPLE 7

15.0% of $Cu(OH)^2.CuCO_3$,
30% of aminoethanolamine,
25.0% of boric acid and
27.0% of $H_2O$
(4% strength aqueous solution).
Amount washed out:
Cu 12.5%
B 88.0%.

EXAMPLE 8

70% of copper borate paste (dispersed in water to give a 50% strength dispersion) and
30% of monoethanolamine
(4% strength aqueous solution).
Amount washed out:
Cu 7.5%
B 85.0%.

EXAMPLE 9

75% of copper borate paste (dispersed in water to give a 50% strength dispersion) and
25% of monoethanolamine
(4% strength aqueous solution).
Amount washed out:
Cu 6.2%
B 66.1%.

COMPARATIVE EXPERIMENT 1

Chromium-containing salts:

| | | |
|---|---|---|
| 1a) | Type CCB | |
| | Cu content | 8.6% |

| | -continued | |
|---|---|---|
| | Chromium-containing salts: | |
| 1b) | Cr content | 13.4% |
| | B content | 4.4% |
| | Type CCF | |
| | Cu content | 7.7% |
| | Cr content | 25.5% |
| | F content | 14.5% |
| Ia) | Type CCB | Amount washed out, in % |
| | Cu | 8.0 |
| | Cr | 2.0 |
| | B | 93.5 |
| Ib) | Type CCF | Amount washed out, in % |
| | Cu | 13.5 |
| | Cr | 18.5 |
| | F | 72.5 |

COMPARATIVE EXPERIMENT 2

(not according to the invention)

12.0% of CuO,
22.0% of ethylenediamine,
12.0% of $KHF_2$ and
54.0% of water
dissolved in water to give a 3% strength solution.
Amount washed out:
Cu 75.5%
F 92.5%.

We claim:

1. A composition for solid wood preservation consisting essentially of a water dilutable formulation of
   (a) from 5 to 50% by weight of an inorganic copper compound,
   (b) from 5 to 50% weight of monoethanolamine,
   (c) from up to 50% by weight of a salt of a fungicidal anion, and
   (d) from up to 5% by weight of free alkali,
   the percentages summing to 100%, with the proviso that when the formulation composition is diluted with water to a wood treatment concentration of about 1 to 5 percent of the non-aqueous components in the aqueous solution, a pH of not less than 8 is established in the resulting aqueous composition.

2. A composition according to claim 1, wherein the inorganic copper compound is selected from the group consisting of copper sulfate, copper fluoroborate, copper hydroxide, copper borate, copper fluoride, copper carbonate and copper oxychloride.

3. A process for preparing a wood impregnating solution which comprises diluting a mixture consisting essentially of: (a) 5 to 50% by weight of an inorganic copper compound, (b) from 5 to 50% by weight of monoethanolamine, (c) up to 50% by weight of a salt of a fungicidal anion, and (d) up to 5% by weight of free alkali,
   with water and adjusting the pH of the resulting aqueous mixture to pH 8 or higher with monoalkanolamine or alkali metal hydroxide.

4. A composition according to claim 1 wherein the fungicidal anion is derived from boric acid or a salt thereof.

* * * * *

UNITED STATES PATENT AND TRADEMARK OFFICE
CERTIFICATE OF CORRECTION

PATENT NO. : 5,078,912
DATED : Jan. 7, 1992
INVENTOR(S) : Reimer GOETTSCHE It is certified that error appears in the above-identified patent and that said Letters Patent is hereby corrected as shown below:

On the Cover Page, Item [22]

The filing date should read --May 1, 1990--

Foreign Application Priority Data is missing. The missing data should read --Jun. 7, 1985 DE Fed Rep of Germany 3520394--

Signed and Sealed this

Eleventh Day of May, 1993

Attest:

MICHAEL K. KIRK

*Attesting Officer*  *Acting Commissioner of Patents and Trademarks*